(12) United States Patent
Cohen et al.

(10) Patent No.: US 9,869,648 B2
(45) Date of Patent: Jan. 16, 2018

(54) HIGH DENSITY GRIDS

(71) Applicant: The Board of Trustees of the Leland Stanford Junior University, Palo Alto, CA (US)

(72) Inventors: Aina E. Cohen, Pacifica, CA (US); Elizabeth L. Baxter, San Jose, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 183 days.

(21) Appl. No.: 14/869,053

(22) Filed: Sep. 29, 2015

(65) Prior Publication Data
US 2016/0019994 A1    Jan. 21, 2016

Related U.S. Application Data

(63) Continuation-in-part of application No. 14/750,470, filed on Jun. 25, 2015, now abandoned.

(60) Provisional application No. 62/017,594, filed on Jun. 26, 2014.

(51) Int. Cl.
*G01N 23/10* (2006.01)
*G01N 23/20* (2006.01)

(52) U.S. Cl.
CPC ....... *G01N 23/20025* (2013.01); *G01N 23/20* (2013.01); *G01N 23/10* (2013.01)

(58) Field of Classification Search
CPC .......................... G01N 23/20; G01N 23/20025

USPC ............................................. 378/73, 79, 208
See application file for complete search history.

(56) References Cited

U.S. PATENT DOCUMENTS

| | | | |
|---|---|---|---|
| 6,296,673 B1 * | 10/2001 | Santarsiero | B01J 19/0046 23/295 R |
| 6,404,849 B1 * | 6/2002 | Olson | G01N 23/20 378/205 |
| 6,507,636 B1 * | 1/2003 | Lehmann | B01L 3/50853 378/208 |
| 6,697,454 B1 * | 2/2004 | Nicolich | G21K 1/06 378/48 |
| 6,719,840 B2 * | 4/2004 | David | C30B 7/00 117/200 |
| 6,818,060 B2 * | 11/2004 | Stewart | C30B 7/00 117/200 |
| 6,860,940 B2 * | 3/2005 | Segelke | B01J 19/0046 117/13 |

(Continued)

OTHER PUBLICATIONS

Elizabeth L. Baxter et al., High-density grids for efficient data collection from multiple crystals, Acta Cryst. (2016). D72, 2-11.*

(Continued)

*Primary Examiner* — Allen C. Ho
(74) *Attorney, Agent, or Firm* — Lumen Patent Firm

(57) ABSTRACT

An X-ray data collection grid device is provided that includes a magnetic base that is compatible with robotic sample mounting systems used at synchrotron beamlines, a grid element fixedly attached to the magnetic base, where the grid element includes at least one sealable sample window disposed through a planar synchrotron-compatible material, where the planar synchrotron-compatible material includes at least one automated X-ray positioning and fluid handling robot fiducial mark.

11 Claims, 7 Drawing Sheets

(56) References Cited

U.S. PATENT DOCUMENTS

| | | | | |
|---|---|---|---|---|
| 6,918,698 B2* | 7/2005 | Nordmeyer | B01L 9/065 | 378/205 |
| 7,008,599 B1* | 3/2006 | Carlton | G01N 1/40 | 422/245.1 |
| 7,144,457 B1* | 12/2006 | McRee | C30B 7/00 | 117/2 |
| 7,162,888 B2* | 1/2007 | Shu | B25J 11/00 | 378/208 |
| 7,263,162 B2* | 8/2007 | Thorne | C30B 29/58 | 250/440.11 |
| 7,292,263 B2* | 11/2007 | Segelke | G02B 21/10 | 348/79 |
| 7,438,472 B1* | 10/2008 | Lazarski | C30B 29/58 | 378/205 |
| 7,660,389 B1* | 2/2010 | Becker | G01N 23/20016 | 378/205 |
| 7,666,259 B2* | 2/2010 | Thorne | C30B 7/04 | 117/68 |
| 7,763,471 B2* | 7/2010 | Pamula | G01N 23/20 | 422/68.1 |
| 7,974,380 B2* | 7/2011 | Fowler | G01N 23/20025 | 378/208 |
| 7,998,436 B2* | 8/2011 | Pollack | C07K 1/1136 | 422/500 |
| 8,440,986 B2* | 5/2013 | Gofron | G01N 23/223 | 250/461.1 |
| 8,636,843 B2* | 1/2014 | Jeong | B82Y 30/00 | 117/104 |
| 8,804,897 B2* | 8/2014 | Pop | G21C 17/017 | 376/305 |
| 9,275,844 B2* | 3/2016 | Bogan | H01J 49/0431 | |
| 9,632,042 B2* | 4/2017 | Ren | G01N 23/207 | |
| 9,731,289 B2* | 8/2017 | Cipriani | C12M 41/48 | |

OTHER PUBLICATIONS

Aina E. Cohen et al., Goniometer-based femtosecond crystallography with X-ray free electron lasers, PNAS vol. 111, No. 48, 17122-17127, 2014.*

Jinhu Song et al., Diffraction-based automated crystal centering, Journal of Synchrotron Radiation (2007). 14, 191-195.*

Tsu-Yi Teng, Mounting of Crystals for Macromolecular Crystallography in a Free-Standing Thin Film, Journal of Applied Crystallography (1990) 23, 387-391.*

* cited by examiner

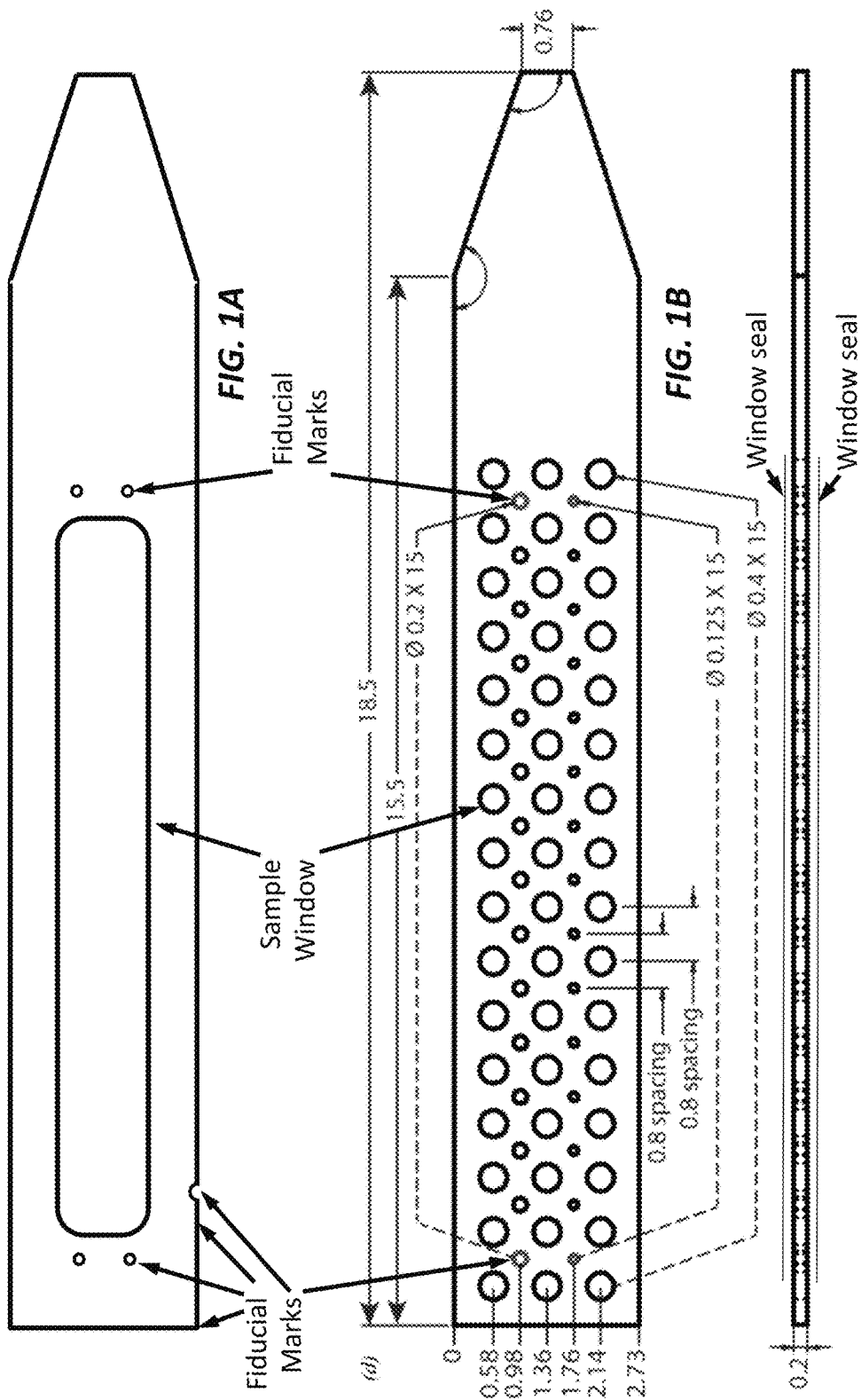

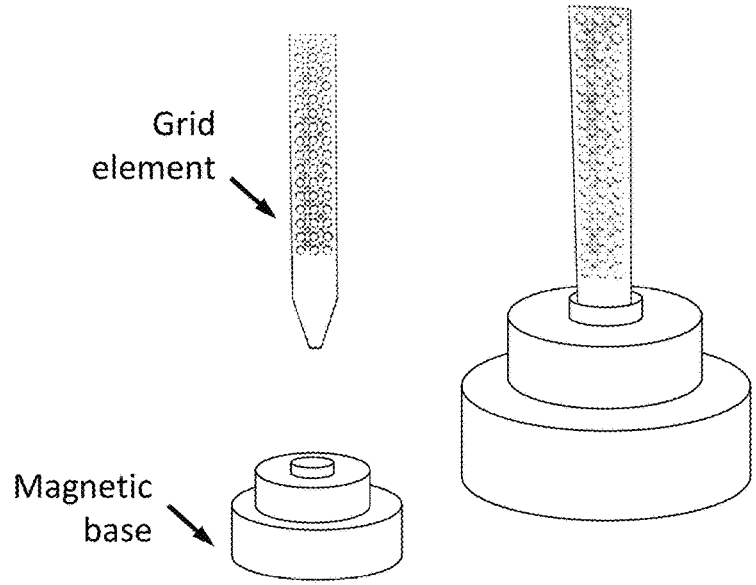
Grid element
Magnetic base
*FIG. 2A*  *FIG. 2B*
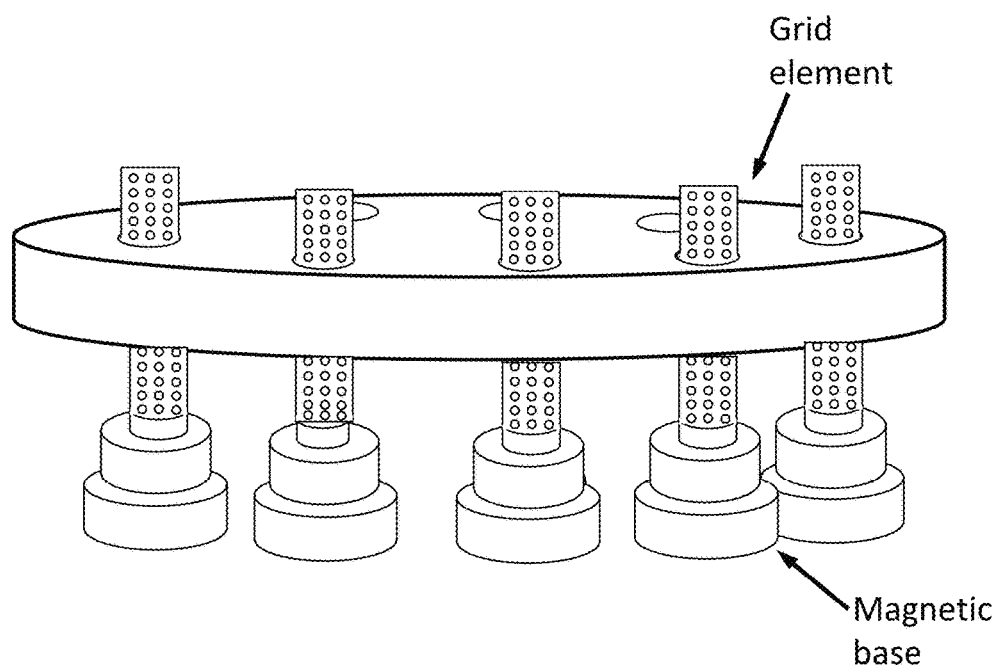
Grid element
Magnetic base
*FIG. 2C*

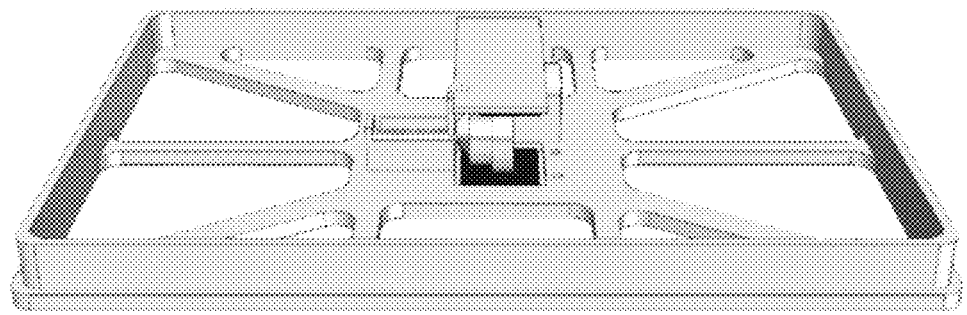
FIG. 6A
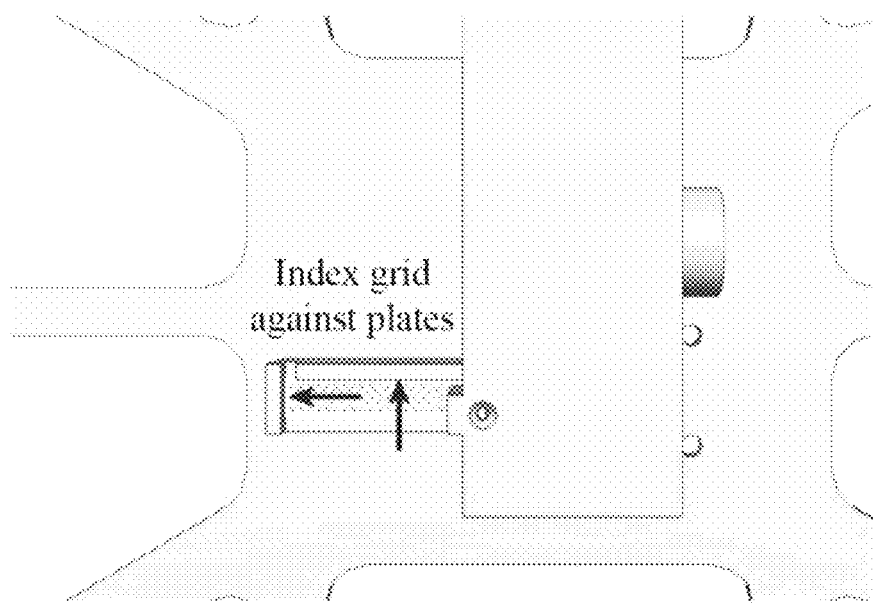
FIG. 6B
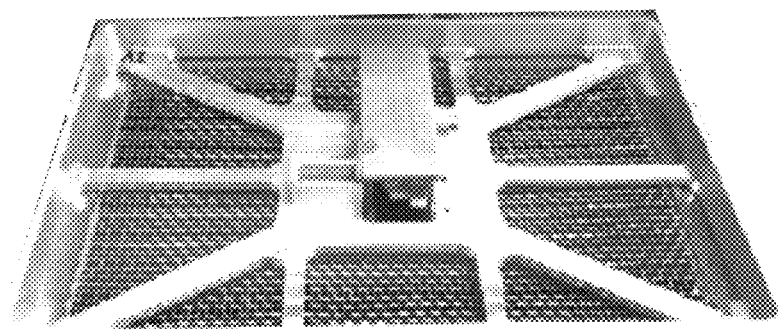

HIGH DENSITY GRIDS

CROSS-REFERENCE TO RELATED APPLICATIONS

This application is a continuation-in-part of U.S. patent application Ser. No. 14/750,470 filed Jun. 25, 2015, which is incorporated herein by reference. U.S. patent application Ser. No. 14/750,470 filed Jun. 25, 2015 claims priority to U.S. Provisional Patent Application 62/017,594, filed Jun. 26, 2014, which is incorporated herein by reference.

STATEMENT OF GOVERNMENT SPONSORED SUPPORT

This invention was made with Government support under contract DE-AC02-76SF00515 awarded by the Department of Energy and under contract GM103393 awarded by the National Institutes of Health. The Government has certain rights in the invention.

FIELD OF THE INVENTION

The present invention relates generally to X-ray data collection and sample preparation for X-ray data collection. More particularly, the invention relates to X-ray sample grids compatible with automated sample mounting systems used at synchrotron beamlines and the magnets used on sample goniometers and positioning stages.

BACKGROUND OF THE INVENTION

As structural biologists tackle ever more challenging systems, the development of efficient methods to deliver large quantities of crystals for X-ray diffraction studies is increasingly important. Proteins that are difficult to crystallize will often produce only small crystals that yield only a few degrees of diffraction data before succumbing to the damaging effects of radiation exposure. For many systems, obtaining a complete dataset to high resolution using very small crystals is possible through the use of microfocus synchrotron beams and the collection and combination of data from multiple crystals. The structural information accessible from very small or very radiation sensitive crystals may be extended through the application of femtosecond crystallography (FX), an emerging method that capitalizes on the extremely bright, short time-scale X-ray pulses produced by X-ray free electron lasers (XFELs). This approach exploits a 'diffraction before destruction' phenomenon where a still diffraction pattern is produced by a single X-ray pulse before significant radiation induced electronic and atomic rearrangements occur within the crystal. Since the area of the crystal exposed to the X-ray pulse is completely destroyed after each shot, multiple crystals are required for these experiments. If larger crystals are available, different areas of the crystal may be exposed to obtain multiple stills from a single crystal. In addition, FX confronts another major challenge in structural enzymology by providing a means to determine catalytically accurate structures of radiation sensitive metalloenzymes, which may undergo structural rearrangement upon photo-reduction of the metal center at a synchrotron. In most cases, these experiments also require a large quantity of samples as each area of the crystal can only be exposed once. High throughput crystallization and the implementation of automated sample mounting systems at synchrotron light sources have made data collection from multiple crystals approachable, however challenges still exist. The process of sample exchange using automated mounting systems, which includes mounting a crystal, centering a crystal for data collection, and dismounting the crystal can take between 35 seconds to a few minutes. While this time scale may be suitable for experiments that require screening of at most a few hundred crystals, higher efficiency methods are required for more challenging endeavors at both the synchrotron and XFEL sources. Furthermore, harvesting crystals for data collection can be another time consuming step. Crystal manipulation robots are being developed to automate this process, however crystal harvesting is still primarily done by hand.

One approach for efficient sample delivery and diffraction quality screening is the use of high-density sample containers that hold crystals in known locations coupled with the use of a high-speed sample goniometer for rapid sample positioning. Examples of high-density sample mounting containers for room temperature data collection include microfluidic chips and micro-crystals traps. What is needed is a simple, inexpensive, high density crystal mounting device for data collection at cryogenic or room temperatures, which is compatible with most automated mounting systems and sample storage containers and enables rapid positioning of multiple crystals.

SUMMARY OF THE INVENTION

To address the needs in the art, an X-ray data collection grid device is provided that includes a magnetic base that is compatible with robotic sample mounting systems used at synchrotron beamlines, a grid element fixedly attached to the magnetic base, where the grid element includes at least one sealable sample window disposed through a planar synchrotron-compatible material, where the planar synchrotron-compatible material includes at least one automated X-ray positioning and fluid handling robot fiducial mark.

In one aspect of the invention, the magnetic base includes a shape that is compatible with sample goniometers disposed at synchrotron beam lines and is compatible with automated sample-pin exchange robotic systems. In one aspect, the magnetic base is compatible with an Advanced Light source (ALS) puck, a uni-puck, an MSC magazine, or a Stanford Synchrotron Radiation Light source (SSRL) cassette. In a further aspect the automated sample-pin exchange robotic systems include SSRL Automated Mounter, ALS Sample Exchange Robot, ACTOR, or a Cryogenic Automated Transfer System (CATS) robotic system.

In another aspect of the invention, the synchrotron-compatible material includes polycarbonate, acrylonitrile butadiene styrene, cyclic olefin copolymer or other polymer material.

According to a further aspect of the invention, the sample window includes a single window, an array of sample holes or an array of the windows, where the array of sample holes or the array of windows comprise a diameter in a range of 50 µm to 2.5 mm.

In yet another aspect of the invention, the fiducial mark includes a hole, a mark, a dimple, a corner or an edge of the planar synchrotron-compatible material. In one aspect, the fiducial mark hole has a diameter in a range of 5 µm to 200 µm.

According to one aspect of the invention, the rectangular planar synchrotron-compatible material includes a thickness in a range of 25 µm to 300 µm.

In a further aspect of the invention, the at least one sealable window includes a transparent sheet that includes of graphene, holey carbon, mylar, polyamide, polyimide film with silicone adhesive, or polymers. In one aspect, the transparent sheet includes a thickness in a range of 100 nm to 20 µm.

BRIEF DESCRIPTION OF THE DRAWINGS

FIGS. 1A-1C show the body of grids having a sheet of polycarbonate with (FIG. 1A) a single sample window, and (FIG. 1B-1C) multiple rows of holes, according to one embodiment of the invention.

FIGS. 2A-2C show the grids affixed into a magnetic base compatible with automated sample mounting systems used at synchrotron beamlines as well as the magnets used on sample goniometers and positioning stages, and the grids affixed to a magnetic base, a specialized jig is used to prevent grids from tilting in the base as glue sets, according to one embodiment of the invention.

FIGS. 6A-6C show a specialized adaptor with an SBS plate compliant footprint used to hold a grid in the destination plate position of liquid handling robots to receive a liquid sample, or solid liquid suspension, according to one embodiment of the invention.

DETAILED DESCRIPTION

The current invention provides an X-ray data collection grid device having a magnetic base that is compatible with robotic sample mounting systems used at synchrotron beamlines, a grid element fixedly attached to the magnetic base, where the grid element includes at least one sealable sample window disposed through a planar synchrotron-compatible material that includes polycarbonate, acrylonitrile butadiene styrene, cyclic olefin copolymer or other polymer material, where the planar synchrotron-compatible material includes at least one automated X-ray positioning and fluid handling robot fiducial mark. The fiducial mark includes a hole, a mark, a dimple, a corner or an edge of the planar synchrotron-compatible material. In one aspect, the fiducial mark hole has a diameter in a range of 5 µm to 200 µm.

According to the invention, the X-ray data collection grid device significantly improves the efficiency of data collection by allowing multiple samples to be mounted simultaneously by the sample mounting robots currently ulitized at synchrotron and XFEL light sources, according to one embodiment. Current automated sample mounting systems mount and dismount a sample in approximately 30 seconds to 2 minutes. In one embodiment, the grid holds 76 samples, meaning that it can save up to approximately 150 minutes of wasted in mounting time. The grid device, according to the current invention, also reduces sample alignment time because all samples contained in a grid undergo the alignment procedure simultaneously. This alignment procedure may be fully automated. Subsequently, grid ports (also referred to as windows) are automatically positioned into the X-ray beam (or measurement position) and data is automatically collected for each grid ports. Depending on the measurement integration time and detector properties, the entire data collection process takes can take from only a few seconds to minutes, where automated screening for 76 samples mounted individually can take several hours. The compact nature of the grid device allows for greater efficiency in storage and transportation of samples. The use of grid devices with SSRL cassettes increases the sample capacity of a cassette from 96 samples to up to 7200 samples (or more).

Figure 5A:
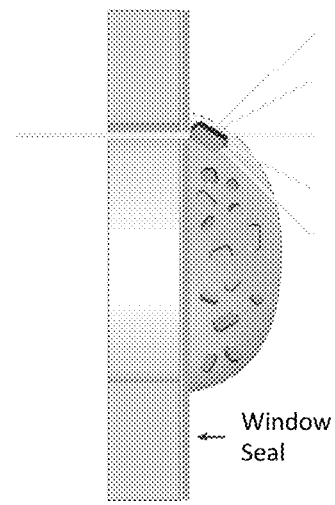
FIGS. 5A-5C show (FIG. 5A) a grid implemented in a hanging drop crystallization experiment, (FIG. 5B) a specialized holder is used to position a grid surrounded by precipitating agent within a glass sandwich to facilitate crystal growth in lipidic cubic phase on the grid, (FIG. 5C) two sheets of window seals placed over the open windows and held in place by capillary action, according to one embodiment of the invention.

In a further embodiment, the current invention also serves as a scaffold for crystal growth. Tools have been developed to enable compatibility with commercial liquid handling robots including the Art Robbins Gryphon and Labcyte Echo550. After protein sample and precipitating agents have been deposited on grids, they may be incubated in specialized crystal growth contains which support hanging or sitting drop experiments and LCP crystallization experiments (see FIG. 5A). By growing crystals directly on the data collection grid device, the crystal harvesting step may be bypassed, which not only saves time, but protects the sample from human handling.

In a further embodiment, the grid device may hold multiple samples in separate ports for X-ray data collection. Samples may include microcrystals, suspensions of crystals, amorphous material, and sample fluids. X-ray data collection may include methods such as diffraction quality screening, X-ray scattering experiments, or X-ray absorption experiments.

Grids allow for higher throughput preparation and screening of protein and small molecule microcrystals. This is critical for reducing the time and cost involved in protein and macromolecular structure determination, the characterization of potential drug leads, and the identification of drug binding sites, for example during fragment based drug design.

According to further embodiments, specialized grid related tools are used to aid in mounting samples in the grid ports, incubating grids in controlled environments, and holding and positioning the grid during X-ray experiments.

An exemplary embodiment of the invention is described and shown herein, where the body of the grid includes a 25 µm to 300 µm thin sheet of polycarbonate with (FIG. 1A) a single sample window, and with multiple rows of holes cut into it, as shown in FIGS. 1B-1C. According to a further aspect of the invention, the sample window can be a single window, an array of sample holes or an array of the windows, where the array of sample holes or the array of windows have a diameter in a range of 50 µm to 2.5 mm. The fiducial mark includes a hole, a mark, a dimple, a corner or an edge of the planar synchrotron-compatible material. In one aspect, the fiducial mark hole has a diameter in a range of 5 µm to 200 µm.

In practice, the grid ports may be filled with liquid, crystals may be mounted in the holes by hand, suspensions of crystals may be loaded in to the holes, by hand using a loop or piettor or, using a liquid handling robot, or crystals may be grown in the holes by loading them with a protein sample and precipitating agent. Samples contained in grids may be stored at room temperature or cryogenic temperatures, where the glue and plastics used to fabricate grids is compatible with room and cryogenic temperatures, according to one embodiment.

The grids are affixed into a magnetic base (such as a stainless steel Hampton-style base) compatible with automated sample mounting systems used at synchrotron beamlines (such as the Stanford SAM system, the ALS robot and the Rigaku ACTOR robot) as well as the magnets used on sample goniometers and positioning stages (FIG. 2A). According to the invention, the magnetic base has a shape that is compatible with sample goniometers disposed at synchrotron beam lines and is further compatible with automated sample-pin exchange robotic systems. In one aspect, the magnetic base is compatible with an ALS puck, a uni-puck, an MSC magazine, or an SSRL cassette. In a further aspect the automated sample-pin exchange robotic systems include S SRL Automated Mounter, ALS Sample Exchange Robot, ACTOR or a CATs robotic system.

Figure 3A:
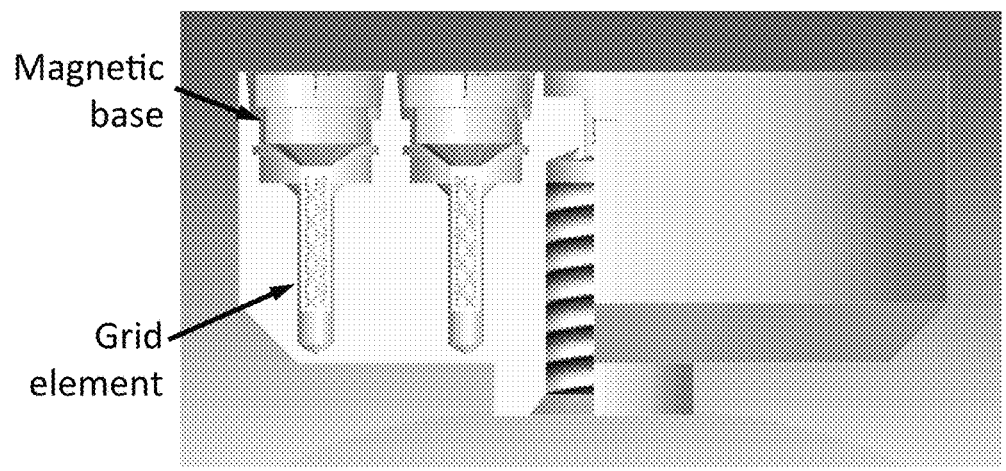
FIGS. 3A-3B show the grids affixed to a magnetic base, the ports of uni-puck enclosures, and SSRL cassettes, according to one embodiment of the invention.
Figure 3B:
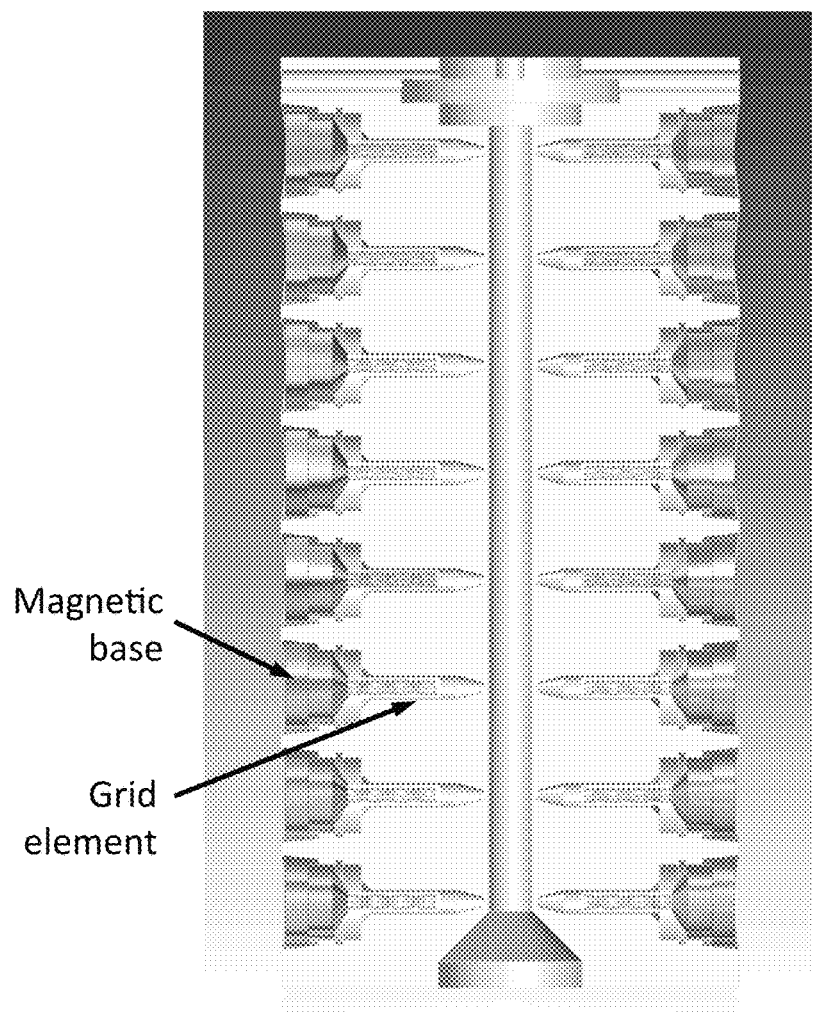

While affixing grids to a magnetic base, a specialized jig may be used to prevent grids from tilting in the base as glue sets (FIG. 2B), according to one aspect of the invention. For example, grids affixed to a Hampton magnetic base fit inside cryotongs, the ports of uni-puck enclosures (FIG. 3A) and SSRL cassettes (FIG. 3B).

Figure 4A:
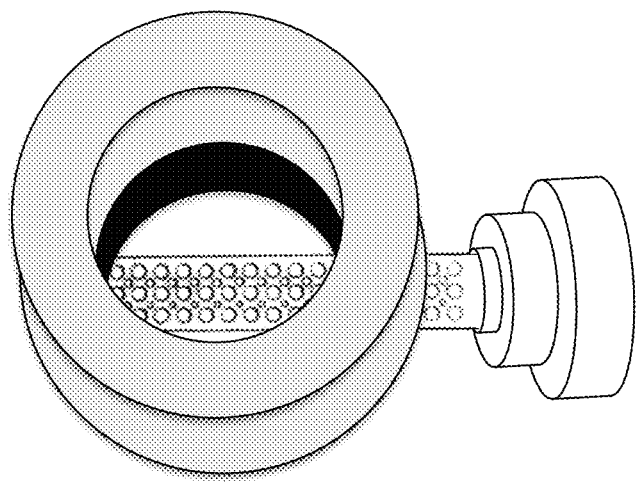
FIGS. 4A-4B show a specialized holder used to store grids at a controlled humidity for crystal growth by vapor diffusion, where the container may be filled with fluids or dessicants to control the grid environment, according to one embodiment of the invention.
Figure 4B:
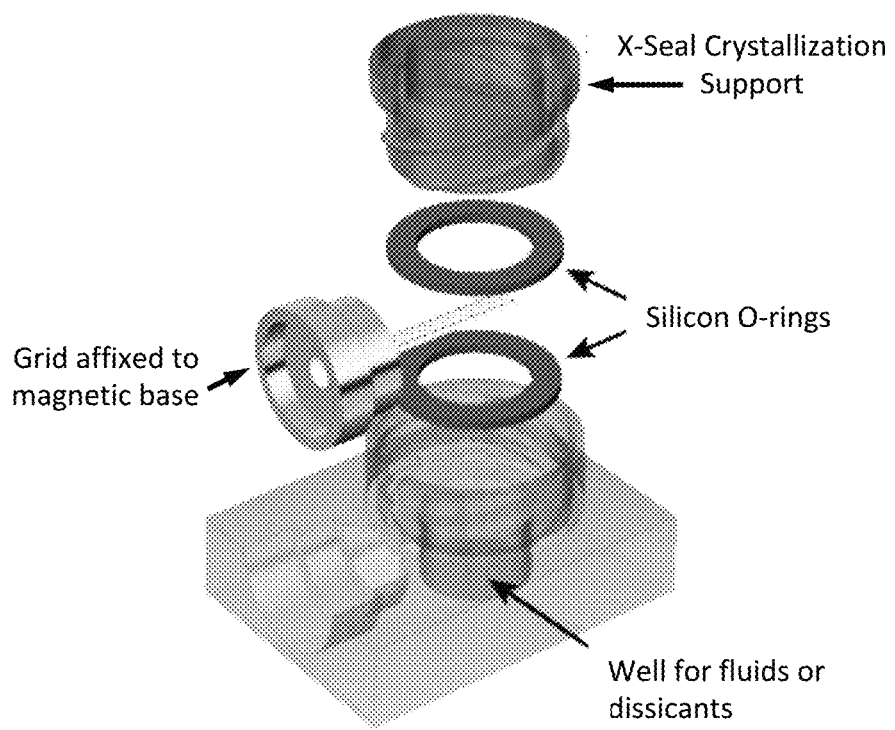

In one embodiment, a specialized holder is used to store grids at a controlled humidity. This is useful for for crystal growth by vapor diffusion, for crystal loading and other experiments. The container may be filled with fluids or dessicants to control the grid environment (FIGS. 4A, 4B).

Figure 5C:
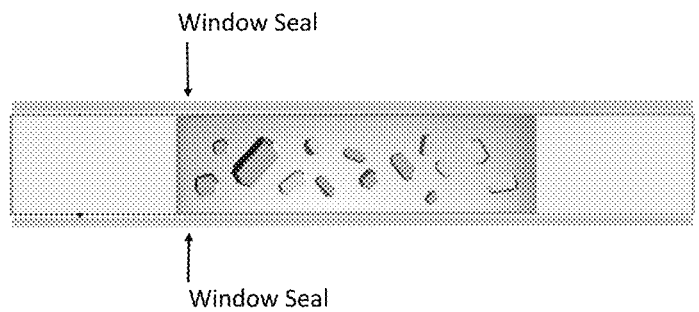
Figure 5B:
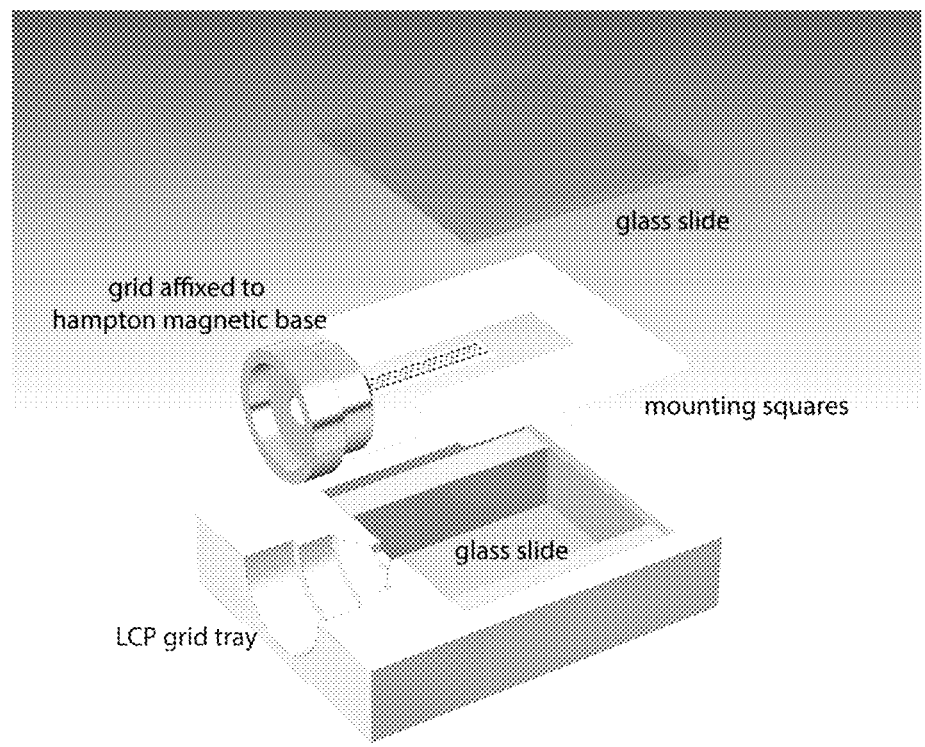
Figure 7A:
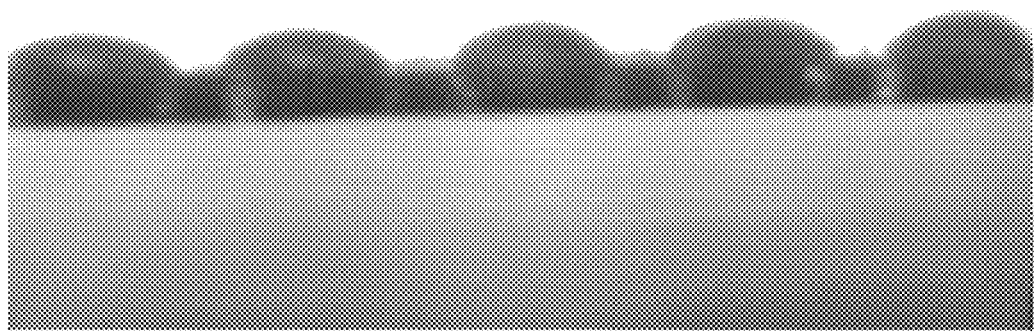
FIGS. 7A-7B show (FIG. 7A) an edge-on view of a grid with polycarbonate backing during data collection at LCLS-XPP, where, according to one embodiment of the invention, an Echo 550 liquid handling robot was used to position droplets of a crystal suspension inline with grid ports immediately prior to flash freezing in liquid nitrogen, and (FIG. 7B) two protein crystals positioned over a grid port during data collection at LCLS-XPP, where hole is clearly visible in the top crystal where it has been exposed to the X-ray beam. The bottom crystal is still intact.
Figure 7B:
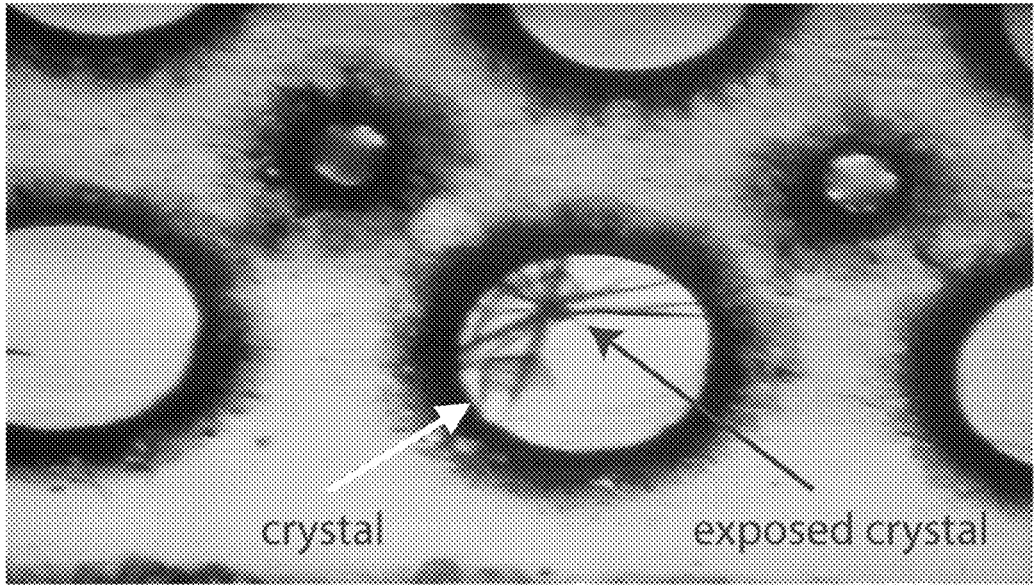

According to one embodiment, a specialized holder is used to position a grid surrounded by precipitating agent within a glass sandwich to facilitate crystal growth in lipidic cubic phase on the grid (FIG. 5B). In a further aspect of the invention, the transparent sheet of the sealable window can be glass, graphene, holey carbon, mylar, polyamide, polyimide film with silicone adhesive, or polymer. In one aspect, the transparent sheet includes a thickness in a range of 100 nm to 20 µm.

In a further embodiment, a specialized adaptor with an SBS plate compliant footprint is used to hold a grid in the destination plate position of liquid handling robots (such as the Labcyte Echo550 or Art Robbins Instruments Gryphon) to receive a liquid sample, or solid liquid suspension (FIGS. 6A-6C). In this example, the grid is indexed against two metal plates protruding from the adaptor so that sample ports are in the correct position to receive sample (FIG. 6B). Further, specialized grid related tools are used to aid in hand mounting samples in the grid ports.

In a further embodiment, routines in a Blu-Ice/DCSS experimental control system are used for semi-automated grid alignment, fully automated positioning of grid ports, rastering, and automated data collection. Crystal positions may be mapped in relation to the grid fiducial marks for subsequent automated centering.

According to other embodiments of the current invention, new features include a mounting device that is both capable of holding multiple samples in separate ports on a single magnetic base, and compact enough to fit within a single port of a uni-puck enclosure or SSRL cassette, and cryotongs. The current invention is both compatible with liquid handling robots, and useful for x-ray diffraction, small angle scattering, or x-ray absorption data collection. The current invention is compatible with a specialized incubation chamber for the growth of crystals directly in the ports of a multiport mounting device, and compatible with a specialized tray, which allows crystals to be grown in lipidic cubic phase directly in the ports of a multiport mounting device within a glass sandwich. Further, the current invention can be used with a specialized holder having indexing plates for the positioning of a multiport mounting device that is pre-glued to a magnetic base in the destination plate position of a liquid handling robot to receive sample, and a automated alignment procedure, which makes use of a grid pattern of sample ports to index sample locations for rapid data collection during x-ray diffraction, small angle scattering, or X-ray absorption experiments. Further, the invention can be used with thin, optically clear, polycarbonate sheeting that results in minimal X-ray absorption and low X-ray scattering background.

The grid element invention enables efficient automated data collection from a large number of crystals that will only survive a few X-ray exposures or small rotational ranges during data collection. Since crystals are held in known locations, rapid and precise automated crystal positioning into the X-ray beam path is possible. In addition, grids may also serve as a scaffold for crystal growth and are compatible with many liquid handling robots, allowing for increased automation in crystal growth and harvesting.

In an exemplary embodiment, the grid scaffold includes of a piece of 100 µm thick polycarbonate plastic with laser cut rows of holes (or ports). This polycarbonate scaffold is affixed to a standard magnetic base to produce the 'grid assembly' (FIG. 1B-1C). A specialized bonding jig is used to hold the polycarbonate scaffold inside the magnetic base as the epoxy sets (FIG. 2A-2B). Grid ports may hold either large crystals, or groups of smaller crystals, in known locations. The current grid layout has 74 ports that can include 400 µm, 200 µm, and 125 µm diameters, along with 4 fiducial markers (FIG. 1B), however the size and arrangement of ports may be altered to better suit different experimental setups. Grids may have an additional thin polymer film affixed to one face to better hold samples within ports, or to serve as a scaffold for sitting or hanging drop crystallization experiments. The 5 µm thick polycarbonate film in this exemplary embodiment has minimal X-ray absorption and low X-ray scattering background.

The grid elements have been used in combination with goniometer based instrumentation installed at the Linac Coherent Light Source (LCLS) X-ray Pump Probe (XPP) station for XFEL diffraction experiments. During these experiments, the Stanford Automated Mounter was used to mount grids containing crystals onto the goniometer. In this example, the size of the grid was maximized to expand the cassette capacity from 96 to more than 7200 sample locations while reliably fitting inside the port of a SSRL cassette (FIG. 2C). Grid assemblies are also compatible with uni-puck storage containers.

To control these experiments, automated routines were added to the experimental control software Blu-Ice/DCSS. To define the position of all grid ports in relation to the X-ray beam position, an automated alignment procedure takes advantage of the predefined spatial arrangement of the laser cut grid ports. This process begins by first defining the position of the edge of the grid by rotating it until it is edge-on in the software video display to move the edge of the grid into the X-ray beam position. If the grid is tilted in this view, two positions may be identified to define the translation path.

Next the grid is rotated by 90 degrees to put the face-on view of the grid. Four ports on the outer corners of the grid are then identified which act as fiducial markers to define the port locations and the grid rotation (FIG. 1B). This procedure calibrates all of the grid ports to the coordinate system of the goniometer and beam interaction region. For crystals that closely match the size of each grid port, data collection may then be carried out automatically; each port is automatically centered into the X-ray interaction region and exposed. Alternatively, automated data collection may be paused and a different area of the port may be selected for exposure using a manual "click-and-shoot" procedure.

Helical data collection may also be setup across longer crystals within grid ports. A spreadsheet, specifying which grid ports contain crystals, may be uploaded in advance so that empty ports are automatically skipped during data collection.

In cases where a group of small crystals is present inside a port, X-ray raster searches may be performed on the entire grid port, or on a smaller area within the port. Rastering is often performed at synchrotrons with low doses of radiation to locate crystals. At an XFEL, a raster mode of data collection is done with a full dose of radiation to collect data from multiple crystals in a grid port, or to collect data from multiple locations on a single crystal. The entire grid port may be rastered automatically using the Blu-ice/DCSS software by using a pull-down menu to choose the port, and a suitable circular area is automatically defined, or a smaller area containing crystals may be rastered by defining the edges of a polygon from within the software display. Moreover, the exact position of small crystals placed randomly within a grid window may be mapped in relation to the fiducial marks prior to data collection using microscopy, or a raster search using low dose X-rays. After running the automated alignment procedure, positioning software applies the crystal map to rapidly position these crystals into the X-ray beam position.

This automation may be further incorporated into automated software workflows for fully automated multi-crystal data collection strategies.

Grids may be manually filled with crystals. Crystals can be viewed during this process by positioning the grid assembly underneath a microscope with the use of a magnetic holder. Grid ports can be prefilled with cryo-protectant oil such as paratone-N, or paraffin to prevent crystal dehydration. A fine needle may be used to apply oil to each grid port. A cryo-loop may be used as a tool to remove a crystal from the crystallization tray, coat the crystal with a thin layer of oil, and then transfer it to an appropriately sized grid port. It is helpful to match the size of the cryo-loop tool to a port size in the grid. Filling all ports in a grid may be impractical because crystals may degrade over time in the cryo-protectant oil. Testing is necessary to determine the maximum timeframe for filling grids with a particular sample and oil. This may be accomplished by filling a grid with crystals and recording the loading time for each port. Diffraction data may then be collected and compared for crystals with known exposure times to the oil. Crystals of myoglobin were mounted in grids in this manner for FX experiments at LCLS XPP. During these experiments, still diffraction patterns were collected from 932 crystals in 32 grids; of these, 739 stills were included in a final dataset that was fully complete to 1.5 Å resolution.

Grid ports may be covered with a thin polymer film or sleeve to prevent evaporation and sample dehydration. This modification enables grids to be used for room temperature data collection of protein crystals in water based cryoprotectants, or other evaporation sensitive samples. This approach was used for room temperature screening of protein crystals at LCLS-XPP. A polycarbonate backing was glued to one face of a grid with epoxy. A suspension of protein crystals was pipetted over the open grid ports, and a loop was used to drag crystals into the ports (FIG. 2A). A second sheet of polycarbonate was placed over the open ports and held in place by capillary action (FIG. 5C). Minimal evaporation was observed over the course of 30 minutes.

Crystals may be grown directly inside grid ports. To fill grids with crystallization solutions for this purpose, an adaptor was developed that holds a grid assembly in the destination plate position of liquid handling robots (FIG. 6A). A neoprene lined torsion clip grips the magnetic base of the grid assembly and holds it in place. Grids are indexed against two metal surfaces to ensure accurate reproducible drop placement (FIG. 6B). The adaptor has been successfully tested with the Labcyte Echo550 (FIG. 6C), the Art Robbins Gryphon, and the TTP Labtech Mosquito. After sample has been deposited on grids, the grids may be incubated in specialized crystal growth containers, which support hanging or sitting drop experiments and LCP crystallization experiments. Liquid handling robots may also be used to dispense suspensions of protein microcrystals, or other solid liquid suspensions into grids.

A grid vapor diffusion chamber was developed to hold a grid in a controlled environment for incubation of sitting or hanging drop crystallization experiments (FIGS. 4A-B). The chambers are capped with transparent X-seal crystallization supports, or sealed with transparent tape so that crystal growth may be monitored with a microscope. Silicone O-rings are used to ensure a tight seal around the grid scaffold (FIG. 4B) or around the pin base. A thin film of vacuum grease may be applied to the O-rings to improve sealing. A well in the base of the chamber holds up to 350 µL of desiccant below the grid. To demonstrate that grids may be used as scaffolds for crystal growth, sitting drop vapor diffusion experiments were set up on grids using lysozyme as a test case. An Echo550 liquid handler was used to dispense drops of protein and precipitant solution onto a grid with a thin polycarbonate backing. Grids were then incubated in a vapor diffusion chamber drop side up, with desiccant for 5 days. Lysozyme crystals grew on the grids, and the Echo550 liquid handler was used to dispense drops of cryo-protectant on top of the crystallization drops.

In instances in which crystals are manually loaded into grids using water based cryoprotectant, vapor diffusion chambers may be used to prevent evaporation of the sample and cryoprotectant. Grids may be positioned in the vapor diffusion chamber during crystal loading, and liquid may be added to the well of the chamber. The chamber may be opened to allow a crystal to be transferred to the grid, and sealed again in between transfers to maintain a humid environment for the grid. This method may be used for protein crystals, as well as for other evaporation sensitive samples. For example this approach was used to load grids with crystals of a large multi-protein-DNA complex. To accomplish this, a grid was coated with cryoprotectant and placed in a vapor diffusion chamber with cryoprotectant solution in the well. Two microscopes were used to aid visualization of the crystallization tray and the grid in the vapor diffusion chamber. Crystals were transferred from the crystallization tray into the grid using cryo-loops. The chamber was loosely sealed between transfers to maintain humidity. The grids were then flash-frozen and used to screen crystals of the protein-DNA complex at both LCLS-XPP and at SSRL beamline 12-2 producing diffraction patterns to 3.3 Å and 3.7 Å resolution.

LCP crystallization experiments may also be performed on grids with the use of a specialized holder that incorporates full grid assemblies, eliminating the need to manually cut glass or plastic crystallization chambers containing crystals for data collection. The tray holds an assembly in which a grid containing cubic phase is incubated in precipitating solution in a glass sandwich (FIG. 5B). The grid LCP tray assembly includes two siliconized glass slides, for example 1 mm thick double sided tape, and a tray with a support for a magnetic base and glass slides. The grid is sandwiched between the two sheets of glass and is surrounded by precipitating agent. To aid in removal, a thin polycarbonate sheet may be laid on top of the grid and under the top glass plate.

Proof of principal LCP crystallization experiments were performed on grids using an adaptation of a protocol for the growth of lysozyme crystals in LCP as a test case. An Art Robbins Gryphon was used to dispense cubic phase into grid ports, and grids were incubated with precipitating agent in the glass sandwich. Lysozyme crystals up to 100 μm in size were observed in grid ports after 16 hours of incubation.

High density sample mounting devices dramatically reduce the amount of time needed for multi-crystal data collection. Data collection of crystals held in loops requires that each crystal be individually mounted on the goniometer, centered in the X-ray beam, and then dismounted. Automated alignment of crystal containing loops can take between 15 to 30 seconds each, depending on the beamline hardware and software. The time required to mount and dismount a sample varies, however even if sample exchange requires 25 seconds, sample exchange, alignment and exposure for 1000 crystals in loops would consume at least 12 hours of beam time. Furthermore, a 1000 samples mounted individually in loops would require 11 SSRL cassettes or 62 uni-pucks for storage. The sample mounting grid enables more than 70 conventionally sized crystals (~100-300 μm in diameter) to be mounted on the goniometer at once, or many thousands of micro-crystals, circumventing much of the time involved in sample exchange. Time is further saved because alignment is performed once for the entire grid, after which the position of each sample location is automatically calculated by the Blu-Ice/DCSS control software. When conventionally sized crystals are used, the use of grids to screen 1000 crystals would reduce the time spent on sample exchange and alignment from about 12 hours to under 1 hour, and a single uni-puck would be sufficient to hold 1000 samples. Additionally, a single grid port may also be filled with multiple micro-crystals, in which case thousands of crystals may be mounted on the goniometer at once.

Since crystals may be grown directly on grids, crystal harvesting may be avoided entirely during room temperature data collection. Plastic sleeves and backings may be used to lessen the effects of evaporation. Grids may alternatively be transferred directly from an incubation chamber to a goniometer outfitted with a humidity controlled air-stream.

The use of grids for screening LCP conditions will be a very powerful tool for enabling researchers to use grids for both the collection of entire datasets and also to screen conditions for subsequent use of LCP injectors.

The present invention has now been described in accordance with several exemplary embodiments, which are intended to be illustrative in all aspects, rather than restrictive.

Thus, the present invention is capable of many variations in detailed implementation, which may be derived from the description contained herein by a person of ordinary skill in the art. For example variations in embodiments of the current invention include the size, number, and position of the grid holes, the size, shape, or thickness of the grids, the use of different plastics to fabricate the grids with different optical properties, the use of different materials to fabricate the grids with different properties regarding the adhesive force exerted on liquids, and the grids may have a thin polycarbonate sheet affixed to one or both sides to better contain sample within grid holes, where thin sheets or membranes of other materials may also be used for this purpose. Further variations include improved methods for affixing a grid to a magnetic base, variations in the materials or specifications of vapor diffusion chambers for grids, variations in the materials or specifications of the LCP grid assembly, and variations in the materials or specifications of the grid adaptor.

All such variations are considered to be within the scope and spirit of the present invention as defined by the following claims and their legal equivalents.

What is claimed:

1. An X-ray data collection grid device, comprising:
   a. a magnetic base, wherein said magnetic base is compatible with robotic sample mounting systems used at synchrotron beamlines;
   b. a grid element fixedly attached to said magnetic base, wherein said grid element comprising a planar synchrotron-compatible material, wherein said grid element comprises at least one sealable sample window disposed through said planar synchrotron-compatible material, wherein said planar synchrotron-compatible material comprises at least one automated X-ray positioning and fluid handling robot fiducial mark.

2. The X-ray data collection grid device of claim 1, wherein said magnetic base comprises a shape that is compatible with sample goniometers disposed at synchrotron beam lines and is compatible with automated sample-pin exchange robotic systems.

3. The X-ray data collection grid device of claim 2, wherein said magnetic base is compatible with an ALS puck, a uni-puck, an MSC magazine, or an SSRL cassette.

4. The X-ray data collection grid device of claim 2, wherein said automated sample-pin exchange robotic systems comprise SSRL Automated Mounter, ALS Sample Exchange Robot, ACTOR, or a CATs robotic system.

5. The X-ray data collection grid device of claim 1, wherein said planar synchrotron-compatible material comprises polycarbonate, acrylonitrile butadiene styrene, cyclic olefin copolymer or other polymer material.

6. The X-ray data collection grid device of claim 1, wherein said at least one sealable sample window comprises a single window, an array of sample holes, or an array of windows, wherein said array of sample holes or said array of windows comprise a diameter in a range of 50 μm to 2.5 mm.

7. The X-ray data collection grid device of claim 1, wherein said at least one automated X-ray positioning and fluid handling robot fiducial mark comprises a hole, a mark, a dimple, a corner or an edge of said planar synchrotron-compatible material.

8. The X-ray data collection grid device of claim 7, wherein said hole has a diameter in a range of 5 µm to 300 µm.

9. The X-ray data collection grid device of claim 1, wherein said planar synchrotron-compatible material comprises a thickness in a range of 25 µm to 300 µm.

10. The X-ray data collection grid device of claim 1, wherein said at least one sealable sample window comprises a transparent sheet selected from the group consisting of graphene, holey carbon, mylar, polyamide, polyimide film with silicone adhesive, and polymers.

11. The X-ray data collection grid device of claim 10, wherein said transparent sheet comprises a thickness in a range of 100 nm to 20 µm.

* * * * *